United States Patent [19]

Rhodes

[11] Patent Number: 5,384,121
[45] Date of Patent: Jan. 24, 1995

[54] METHOD FOR THE EXTRACTION OF SESQUITERPENE LACTONES

[75] Inventor: Alan Rhodes, Cambridgeshire, United Kingdom

[73] Assignee: Rhodes Technology, Cambridgeshire, United Kingdom

[21] Appl. No.: 87,672

[22] PCT Filed: Jan. 8, 1992

[86] PCT No.: PCT/GB92/00036
§ 371 Date: Jul. 8, 1993
§ 102(e) Date: Jul. 8, 1993

[87] PCT Pub. No.: WO92/11857
PCT Pub. Date: Jul. 23, 1992

[30] Foreign Application Priority Data

Jan. 11, 1991 [GB] United Kingdom ............... 9100581

[51] Int. Cl.$^6$ .................. A61K 35/78; A61K 31/34
[52] U.S. Cl. ............................ 424/195.1; 514/468
[58] Field of Search ............................. 514/468

[56] References Cited

U.S. PATENT DOCUMENTS 4,758,433 7/1988 Johnson et al. ............... 424/195.1

FOREIGN PATENT DOCUMENTS 0098041 1/1984 European Pat. Off. .
2124486 2/1984 United Kingdom .

OTHER PUBLICATIONS

Banthorpe, et al. *Chem. Abstracts 114*, (1991) p. 412, No. 49417c "Parthenolide and other volatiles in the flowerheads of *Tanacetum parthenium* (L.) Schultz Bip.".

Hausen, et al. *Chem. Abstracts 115*, (1991) p. 534 No. 155015a "A simple method of isolating parthenolide from *Tanacetum* and other sensitizing plants".

Hausen, Björn *Contact Dermatitis 24*, (1991) pp. 153–155 "A simple method of isolating parthenolide from *Tanacetum* and other sensitizing plants".

Banthorpe, et al. *Flavor and Fragrance Jour. 5*, (1990) pp. 183–185 "Parthenolide and other volatiles in the flowerheads of *Tanacetum parthenium* " (L.) Schultz Bip.

Chem. Abst. 114(6): 49417c 1991.
Chem. Abst 114(15) 155015A; 1991.
Contact Dermattis 24 (2): 153–155, 1991.

*Primary Examiner*—John W. Rollins
*Assistant Examiner*—Howard C. Lee
*Attorney, Agent, or Firm*—Jan P. Brunelle; Walter H. Dreger

[57] ABSTRACT

The present invention relates to a method for the extraction of sesquiterpene lactones from the plant *Tanacetum parthenium* specifically using polar organic solvents and the use of such extracts in pharmaceutical products. It has been found that by utilization of an extraction procedure in accordance with the current invention, a significantly greater amount of the sesquiterpene lactone parthenolide is extracted from *Tanacetum parthenium* than is the case when using petroleum spirit as the primary extractant, the solvent usually used in previous studies.

4 Claims, No Drawings

METHOD FOR THE EXTRACTION OF SESQUITERPENE LACTONES

The present invention relates to a method for the extraction of sesquiterpene lactones from the plant *Tanacetum parthenium* specifically using polar organic solvents and the use of such extracts in pharmaceutical products.

The plant *Tanacetum parthenium* (feverfew), formerly called *Chrysanthemum parthenium* and also known as Midsummer Daisy, Featherfew, Featherfoil, Flitwort and Bachelor's Buttons, has a traditional reputation for treating a variety of conditions. Those claimed most regularly are migraine and arthritic conditions.

U.K. Patent No 2124486B describes an oil or non-polar solvent extraction of a spasmolytically active composition which comprises a sesquiterpene lactone-containing extract from the plant *Tanacetum parthenium* and its use in the treatment of migraine, asthmatic, bronchial or arthritic conditions.

Currently, the only preparations of feverfew commercially available are tablets or capsules containing dried, powdered or comminuted portions of the plant. These can be obtained through pharmacies and health shops as herbal medicines. However, these preparations vary in the part of the plant used and in the stated feverfew content.

A crude plant material will of course, contain many substances which are not of benefit for the treatment under consideration and which, in addition may have the potential to elicit side effects. Moreover, although the dose of crude material can be defined, this will probably not be equivalent to a uniform dose of the active material, whatever this active material may be.

Attempts have been made to identify the principle and principally active compound from feverfew. Bohlmann and Zdero (Sesquiterpene Lactones and other constitutents from *Tanacetum parthenium*, Phytochemistry 1982; 21: 2543–49) reported that following petrol extraction of aerial parts of the plant the major component identified was the sesquiterpene lactone parthenolide. U.K. Patent No. 2124486B identifies parthenolide as the major component with spasmolytic activity. In 1986 Groenwegen et al (J. Pharm. Pharmacol. 1986; 38:709–712) reported their identification of the constituents of feverfew extracts in relation to their anti-secretory activity, where parthenolide represents 22% of the active material.

The above work has demonstrated that there is a preponderence of potentially active material found within the leaves of *Tanacetum parthenium*. In vitro pharmacological activity studies suggest that medicinal activity is shown by the compounds known as sesquiterpene lactones, particularly parthenolide.

It would therefore be of benefit to further investigate the identity of the active constituents of feverfew and to develop a pharmaceutically acceptable product which retains the medicinal activity of the feverfew plant but in a more refined form than is present in currently commercially available preparations.

Accordingly, the present invention provides a method for the preparation of a sesquiterpene lactone-containing extract of *Tanacetum parthenium* which comprises treating *Tanacetum parthenium* with a polar organic solvent.

The sesquiterpene lactone is derived from the plant *Tanacetum parthenium* by a process comprising contacting the plant tissue in a polar organic solvent for example acetonitrile, methanol, ethanol, isopropanol, ether, ethyl acetate, acetone or a mixture thereof. Ethanol is the preferred solvent, since it is the least toxic with regards to the residues being left in the final product.

Generally the mixture of plant tissue and polar organic solvent will be left to stand, thereby allowing the extraction to take place. Alternatively, the plant tissue may be exhaustively extracted with a polar organic solvent in a Soxhlet apparatus or the like. The plant tissue which is extracted in the method of the invention may be fresh, frozen or dried and may be in comminuted form. The extract is then generally separated from the plant tissue and the solvent removed from the solvent extract by conventional techniques. Following removal of the solvent the remaining primary extract may be further purified by known techniques such as column chromatography and/or recrystallisation and/or further solvent extraction. The remaining plant tissue may be further extracted using the same or an alternative solvent.

The primary extract may alternatively be utilised as the active material for further processing into a finished pharmaceutical preparation. For example the material may be mixed with such tabletting excipients as are known in the art and processed to obtain tablets. In this way it can be seen that reasonably large doses of feverfew may be contained Within relatively small unit dose preparation. These would have the advantage of being more elegant and palatable than those currently commercially available which contain the dried crude vegetable matter.

Surprisingly it has been found that by utilizing an extraction procedure in accordance with the current invention a significantly greater amount of the sesquiterpene lactone parthenolide is extracted from *Tanacetum parthenium* than is the case when using petroleum spirit as primary extractant, which appears to have been the solvent usually used in previous studies. In addition, when using ethanol as the solvent, it has been found that camphor, which has previously been identified as a major constituent of petrol extracts of Feverfew, does not appear to be present. This is very surprising in view of the high solubility of camphor in ethanol and is a beneficial feature of the present invention, due to the irritant nature of camphor in pharmaceutical products.

Previous herbal remedies based on the use of feverfew have usually advised the use of the leaves of the plant for medicinal activity. It was therefore also surprising to discover that the parthenolide content of the flowers of the plant tend to be the same or greater than that of the leaves. Conversely, it was also found that the stalk tissue of the plant contains very little parthenolide.

A primary extract of *Tanacetum parthelium* designed to contain a maximal quantity of sesquiterpene lactones, especially parthenolide, is therefore preferentially prepared using the leaves and flowers of the plant as starting material.

Previous extractions of *Tanacetum parthenium* have identified many compounds present with anti-secretory and spasmolytically effective activity. The sesquiterpene lactone parthenolide (a germacranolide) appears to be the active ingredient having the greatest abundance in *Tanacetum parthenium*.

The chemical structure of parthenolide is:

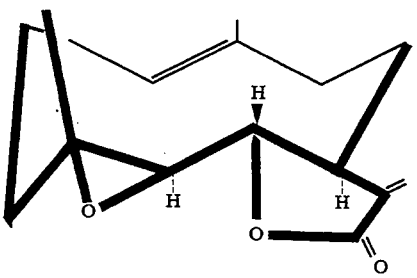

A pharmaceutically active composition comprising a sesquiterpene lactone may be prepared from *Tanacetum parthenium* and administered solely as a plant extract. However, its pharmaceutical efficacy and popularity are generally increased by the addition of a pharmaceutically acceptable excipient.

In addition to the primary or a further refined extract the final pharmaceutical composition may incorporate other components such as bronchodilators (adrenoceptor stimulants, anti-muscarinic bronchodilators, theophylline or compound bronchodilator preparations), anti-histamines (promethazine, trimeprazine, dimenhydrinate, chlorpheniramine, cyclizine, mequitazine, acrivastine, astemizole, cinnarizine, loratadine or terfenadine) or anti-infective agents (anti-fungal, anti-vital or anti-bacterial agents).

For the treatment of migraine the composition may include, in addition to the sesquiterpene lactone, known anti-migraine preparations (aspirin, paracetamol, ergotamine, dihydroergotamine, metoclopramide, isometheptene mucate, clonidine hydrochloride, methysergide or pizotifen), other analgesics (non-opoid analgesics, opoid analgesics or compound analgesic preparations) and/or anti-emetics (hyoscine, anti-histamines, phenothiazines, metoclopramide or clomperidone).

A composition containing any of the above-identified compounds may additionally include other anti-arthritic agents: non-steroidal anti-inflammatory drugs, e.g. naproxen, fenbufen, ketoprofen, aspirin and other salicylates; systemic corticosteroids and corticotrophin e.g. prednisolone; gold, penicillamine, anti-malarials, immuno-suppressants and sulphasalazine.

The sesquiterpene lactone-containing extract in any form may be prepared in the form of a tablet, capsule or liquid suspension for administration either orally, rectally, parenterally or by inhalation.

In one general embodiment of the present invention, the extraction of 1kg of dried comminuted Feverfew can be accomplished by three extracts of 5,3 and 3 liters of ethanol. The combined extracts can then be distilled in order to concentrate the extract at least twenty time without the parthenolide exceeding its solubility limit.

The invention will now be described in greater detail by way of the following specific examples.

EXAMPLE 1

Ether Extraction

Feverfew (490g) was extracted with 2 liters of ether in a Winchester bottle which was maintained at room temperature for 5 days. The ether was poured out, filtered and evaporated in vacuo, whilst maintaining the temperature below 40° C. The residue was partially purified by column chromatography to give parthenolide (2.7 g), impure by thin layer chromatography. Further chromatography, eluting with 40°-60° C. petrol—ethyl acetate as a 3:2 mixture, gave 1.45 g, essentially one spot on the thin layer chromatogram. This material (1.45 g) was dissolved in ether (approximately 25 ml), filtered and the volume reduced to 10 ml. After the solution had been chilled overnight the crystals that had separated were filtered off and washed with cold ether (approximately 10ml). Yield of parthenolide 0.74 g (slight green tint), m.p. 112°-113° C. (lit. 116.5°-117° C.). This sample had the same Rf on a silica gel chromatogram as parthenolide using ether or 40°-60° C. petrol—ethyl acetate in a 3:2 mixture.

Removal of the solvent from the filtrate left a residue of 0.60 g.

EXAMPLE 2

Acetonitrile Extraction

Feverfew (496 g) was extracted with 2 liters of acetonitrile as described in Example 1. Removal of the solvent left a residue of 30.0 g, which was chromatographed with 40°-60° C. petrol—ethyl acetate in a 3:2 mixture, as eluent. The product (1.7 g) was crystallised from ether (15 ml) to give slightly coloured parthenolide (1.02 g). Recrystallisation from ether (15 ml) produced colourless crystals (0.72 g), m.p. 113°-114° C.

EXAMPLE 3

The quantity of parthenolide extracted from samples of dried comminuted feverfew leaves using various solvents was determined using a sensitive high pressure liquid chromatographic analytical procedure.

The results are given in Table 1 below:

TABLE 1

| Amount (mg) of parthenolide extracted from 100 mg portions of dried comminuted feverfew leaves | | | |
|---|---|---|---|
| Solvent | 1st Extract (5 ml) | 2nd Extract (5 ml) | Total |
| Petroleum spirit extract (non-polar organic solvent for comparison) | 0.22 | 0.12 | 0.34 |
| Water (Polar inorganic solvent for comparison) | 0.24 | 0.15 | 0.39 |
| Isopropyl alcohol (Polar organic solvent) | 0.59 | 0.29 | 0.88 |
| Acetonitrile (Polar organic solvent) | 0.66 | 0.17 | 0.83 |

EXAMPLE 4

The parthenolide contents of methanol extracts of 1 g portions of various feverfew tissues were assessed using a sensitive high pressure liquid chromatographic analytical procedure. The results are given in Table 2 below.

TABLE 2

| Amount (mg) of parthenolide extracted into methanol from 1 g portions of various feverfew tissues | | | |
|---|---|---|---|
| Tissue | 1st Extract (100 ml) | 2nd Extract (100 ml) | Total (mg) |
| Leaves | 4.3 | 0.2 | 4.5 |
| Flowers | 14.6 | 0.6 | 15.2 |
| Stalks | 0.2 | — | 0.2 |

I claim:

1. A method for the preparation of a sesquiterpene lactone-containing extract of *Tanacetum parthenium* which comprises treating *Tanacetum parthenium* with a solvent selected from the group consisting of methanol, ethanol, isopropanol, and mixtures thereof.

2. A method as claimed in claim 1 wherein the sesquiterpene lactone is purified by differential extraction.

3. A method as claimed in claim 1 wherein the *Tanacetum parthenium* tissue treated is selected from the group consisting of flower, leaf and a combination thereof.

4. A method as claimed in claim 1 wherein the sesquiterpene lactone extracted is parthenolide.

* * * * *